(12) United States Patent
Gordon

(10) Patent No.: US 6,349,232 B1
(45) Date of Patent: Feb. 19, 2002

(54) APPARATUS AND METHOD FOR DISPENSING PET CARE SUBSTANCES

(75) Inventor: Tal Gordon, Tel Aviv (IL)

(73) Assignee: Pets 'N People Ltd., Tel Aviv (IL)

( * ) Notice: Subject to any disclaimer, the term of this patent is extended or adjusted under 35 U.S.C. 154(b) by 0 days.

(21) Appl. No.: 09/462,634

(22) PCT Filed: Jun. 15, 1999

(86) PCT No.: PCT/IL98/00325

§ 371 Date: Jan. 11, 2000

§ 102(e) Date: Jan. 11, 2000

(87) PCT Pub. No.: WO99/02208

PCT Pub. Date: Jan. 21, 1999

(30) Foreign Application Priority Data

Jul. 11, 1997 (IL) .................................................. 121286

(51) Int. Cl.⁷ .................................................. A61N 1/30
(52) U.S. Cl. .......................... 604/20; 604/132; 604/65
(58) Field of Search .............................. 604/67, 69, 70, 604/130, 140, 147, 154, 156, 891.1, 132, 65, 20, 153, 142, 114; 222/92, 93, 56, 639, 146.1

(56) References Cited

U.S. PATENT DOCUMENTS

| | | |
|---|---|---|
| 3,692,027 A | 9/1972 | Ellinwood ............... 604/891.1 |
| 3,763,859 A | 10/1973 | Yanof et al. |
| 3,768,472 A | 10/1973 | Hodosh et al. |
| 3,852,416 A | 12/1974 | Grubb et al. |
| 4,114,619 A | 9/1978 | Wagner |
| 4,335,835 A | 6/1982 | Beigler et al. |
| 4,360,019 A | 11/1982 | Portner et al. |
| 4,505,710 A | 3/1985 | Collins |
| 4,564,363 A | 1/1986 | Bagnall et al. ........... 604/891.1 |
| 4,652,261 A | 3/1987 | Chapman et al. ......... 604/69 X |
| 4,725,271 A | 2/1988 | Korol |
| 4,735,619 A | 4/1988 | Sperry et al. |
| 4,748,938 A | 6/1988 | Owen |
| 4,803,956 A | 2/1989 | Corrigan et al. |
| 4,890,580 A | 1/1990 | Owen et al. |
| 4,981,104 A | 1/1991 | Goodwin |
| 5,003,756 A | 4/1991 | Mazzotta, Sr. |
| 5,049,141 A | 9/1991 | Olive ...................... 604/891.1 |
| 5,160,320 A | 11/1992 | Yum et al. |
| 5,167,625 A | 12/1992 | Jacobsen et al. |
| D332,409 S | 1/1993 | Magolan |
| 5,224,901 A | 7/1993 | Dahl et al. |
| 5,307,764 A | 5/1994 | Moy |
| 5,405,614 A | 4/1995 | D Angelo et al. |
| 5,411,737 A | 5/1995 | Hsu et al. |
| 5,449,517 A | 9/1995 | Fitzjarrell |
| 5,454,350 A | 10/1995 | Betheil |
| 5,465,689 A | 11/1995 | Winder |
| 5,469,814 A | 11/1995 | Moy et al. |
| 5,472,403 A | 12/1995 | Cornacchia et al. |
| 5,509,859 A | 4/1996 | Klees et al. |
| 5,515,033 A | 5/1996 | Matarazzo |
| 5,516,761 A | 5/1996 | Choi et al. |
| 5,545,442 A | 8/1996 | Van Savage et al. |
| 5,782,799 A | 7/1998 | Jacobsen et al. |
| 5,860,957 A | * 1/1999 | Jacobsen et al. ............ 604/156 |

* cited by examiner

Primary Examiner—Anhtuan T. Nguyen
(74) Attorney, Agent, or Firm—Nixon & Vanderhye P.C.

(57) ABSTRACT

Apparatus for timed dispensing of animal care substances to animals including an electronic dispensing controller, and a dispenser operated by the electronic dispensing controller for dispensing an animal care substance to an animal at times determined by the electronic dispensing controller.

13 Claims, 11 Drawing Sheets

FIG. 21B

APPARATUS AND METHOD FOR DISPENSING PET CARE SUBSTANCES

FIELD OF THE INVENTION

The present invention relates to pet care apparatus and methods generally and more particularly to apparatus and methods for dispensing pet care substances to pets.

BACKGROUND OF THE INVENTION

Various techniques and devices are currently employed for applying pet care substances to pets. Various types of pet collars are described in the following U.S. Patents which were found in a U.S. Patent search: U.S. Pat. Nos. 5,516,761; 5,465,689; 5,449,517; 5,411,737; 5,003,756; 4,981,104; 4,890,580; 4,748,938; 4,224,901; 5,515,033; 5,509,859; 5,469,814; 5,454,350; 5,307,764; 4,803,956; 4,725,271; 5,545,442; 4,725,271; 3,852,416 and Des. 332,409.

SUMMARY OF THE INVENTION

The present invention seeks to provide improved apparatus and methods for dispensing pet care substances to pets. It is noted that throughout the specification and the claims the terms pet and animal are used interchangeably and are understood to be synonymous. It is also understood that although the present invention is described herein generally for use with a pet, nevertheless the present invention is equally applicable for human beings.

There is thus provided in accordance with a preferred embodiment of the present invention apparatus for timed dispensing of pet care substances to pets including an externally pet mounted electronic dispensing controller, and a dispenser operated by the electronic dispensing controller for dispensing a pet care substance to a pet at times determined by the electronic dispensing controller.

Further in accordance with a preferred embodiment of the present invention the apparatus also includes a supply of a pet care substance.

Moreover in accordance with a preferred embodiment of the present invention the pet care substance is enclosed in a single-use, replaceable container.

Still further in accordance with a preferred embodiment of the present invention the dispenser includes a peristaltic pump. Alternatively the dispenser includes a diaphragm pump.

Additionally in accordance with a preferred embodiment of the present invention the dispenser includes a plurality of discrete container cells, each containing the pet care substance, and release apparatus, responsive to the electronic dispensing controller, for selectably releasing the pet care substances from individual ones of the container cells in a desired timed pattern, determined by the electronic dispensing controller.

Further in accordance with a preferred embodiment of the present invention the release apparatus includes an electrical resistance heating element associated with each of the container cells and operative, when energized, to cause at least a portion of the container cell to become permeable for passage therethrough of the pet care substance.

Still further in accordance with a preferred embodiment of the present invention the apparatus includes a collar onto which the electronic dispensing controller and the dispenser are mounted.

Additionally in accordance with a preferred embodiment of the present invention the apparatus also includes a harness onto which the electronic dispensing controller and the dispenser are mounted.

Moreover in accordance with a preferred embodiment of the present invention the apparatus also includes a leg bracelet onto which the electronic dispensing controller and the dispenser are mounted.

Still further in accordance with a preferred embodiment of the present invention the dispenser is operative to dispense the pet care substance onto a pet at a generally dorsal location thereon.

Additionally in accordance with a preferred embodiment of the present invention the dispenser includes an outlet element which directs the pet care substance directly onto the skin of the pet and includes an outlet element which positions the pet care substance such that it can be licked by the pet.

Still further in accordance with a preferred embodiment of the present invention the dispenser includes an outlet element which injects the pet care substance into the pet.

Further in accordance with a preferred embodiment of the present invention the pet care substance may include an anti-parasitic agent, a pet grooming material, an veterinary therapeutic agent and a male animal repellent.

Additionally in accordance with a preferred embodiment of the present invention the dispenser provides continuous application of the pet care substance to the pet. Alternatively the dispenser provides discontinuous application of the pet care substance to the pet.

Still further in accordance with a preferred embodiment of the present invention the electronic dispensing controller is responsive to at least one input produced by the pet.

Additionally in accordance with a preferred embodiment of the present invention the apparatus employs a pet driven power generator for operating, at least one of the controller and the dispenser.

Moreover in accordance with a preferred embodiment of the present invention the apparatus also includes an electronic data storage facility.

Further in accordance with a preferred embodiment of the present invention the apparatus also includes an annunciator associated with the data storage facility for providing an audio output indication responsive to data stored in the electronic data storage facility.

Still further in accordance with a preferred embodiment of the present invention the annunciator provides prompts in response to timing data stored in the electronic data storage facility.

Moreover in accordance with a preferred embodiment of the present invention the annunciator provides lost pet information.

Additionally in accordance with a preferred embodiment of the present invention the annunciator provides normative inputs to the pet.

Still further in accordance with a preferred embodiment of the present invention the apparatus includes a pet communicator which provides at least one way communication with the pet.

Additionally in accordance with a preferred embodiment of the present invention the apparatus includes a pet access controller.

There is also provided in accordance with a preferred embodiment of the present invention a method of pet care including mounting onto a pet, apparatus for timed dispensing of a pet care substance including, an externally pet mounted electronic dispensing controller, and a dispenser operated by the electronic dispensing controller for dispensing a pet care substance to a pet at times determined by the electronic dispensing controller, setting the timing of the apparatus for timed dispensing in accordance with a desired dispensing regime, and supplying the pet care substance to the dispenser.

There is also provided in accordance with a preferred embodiment of the present invention a method for use in pet care including mounting onto a pet, apparatus for timed dispensing of a pet care substance, including an externally pet mounted electronic dispensing controller, and a dispenser operated by the electronic dispensing controller for dispensing a pet care substance to a pet at times determined by the electronic dispensing controller, setting the timing of the apparatus for timed dispensing in accordance with a desired dispensing regime, and supplying the pet care substance to the dispenser, a pet care substance packaged so as to be useful with the dispenser.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
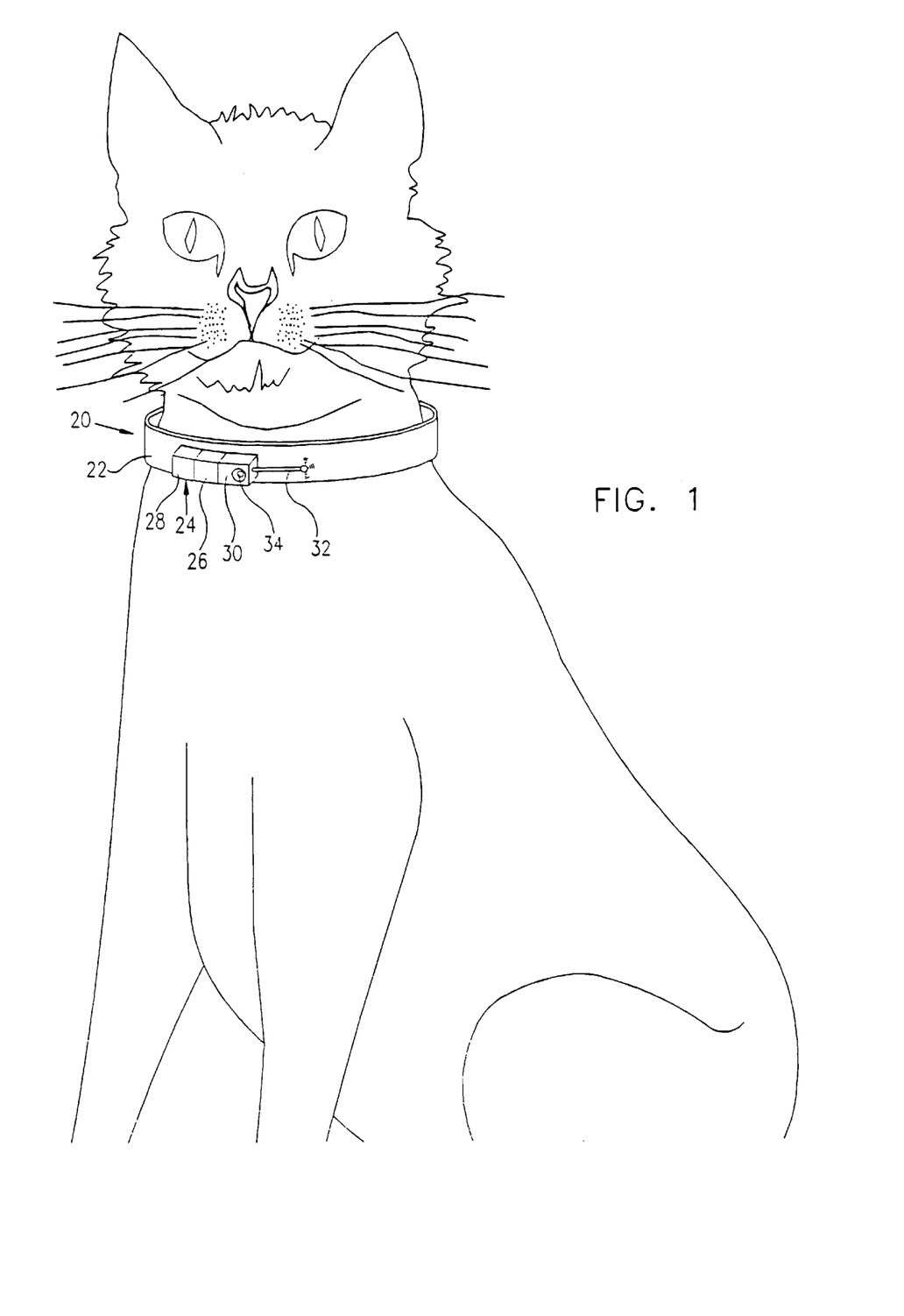
FIG. 1 is a simplified pictorial illustration of a cat wearing a collar constructed and operative in accordance with a preferred embodiment of the present invention.

Reference is now made to FIG. 1, which is a simplified pictorial illustration of a cat wearing a collar 20 constructed and operative in accordance with a preferred embodiment of the present invention. The collar 20 preferably comprises a conventional strap 22 which is fastened about the neck of the cat by conventional means.

In accordance with a preferred embodiment of the invention there is mounted on the strap 22, apparatus 24 for timed dispensing of a pet care substance including an externally pet mounted electronic dispensing controller 26 and a dispenser 28 operated by the electronic dispensing controller 26 for dispensing a pet care substance to the cat at times determined by the electronic dispensing controller 26. In accordance with a preferred embodiment of the present invention, the collar 20 may also include a communication unit 30 including an antenna 32 for permitting wireless communication with the cat and an audio transducer 34, such as a miniature speaker, for providing an audio interface.

Figure 2:
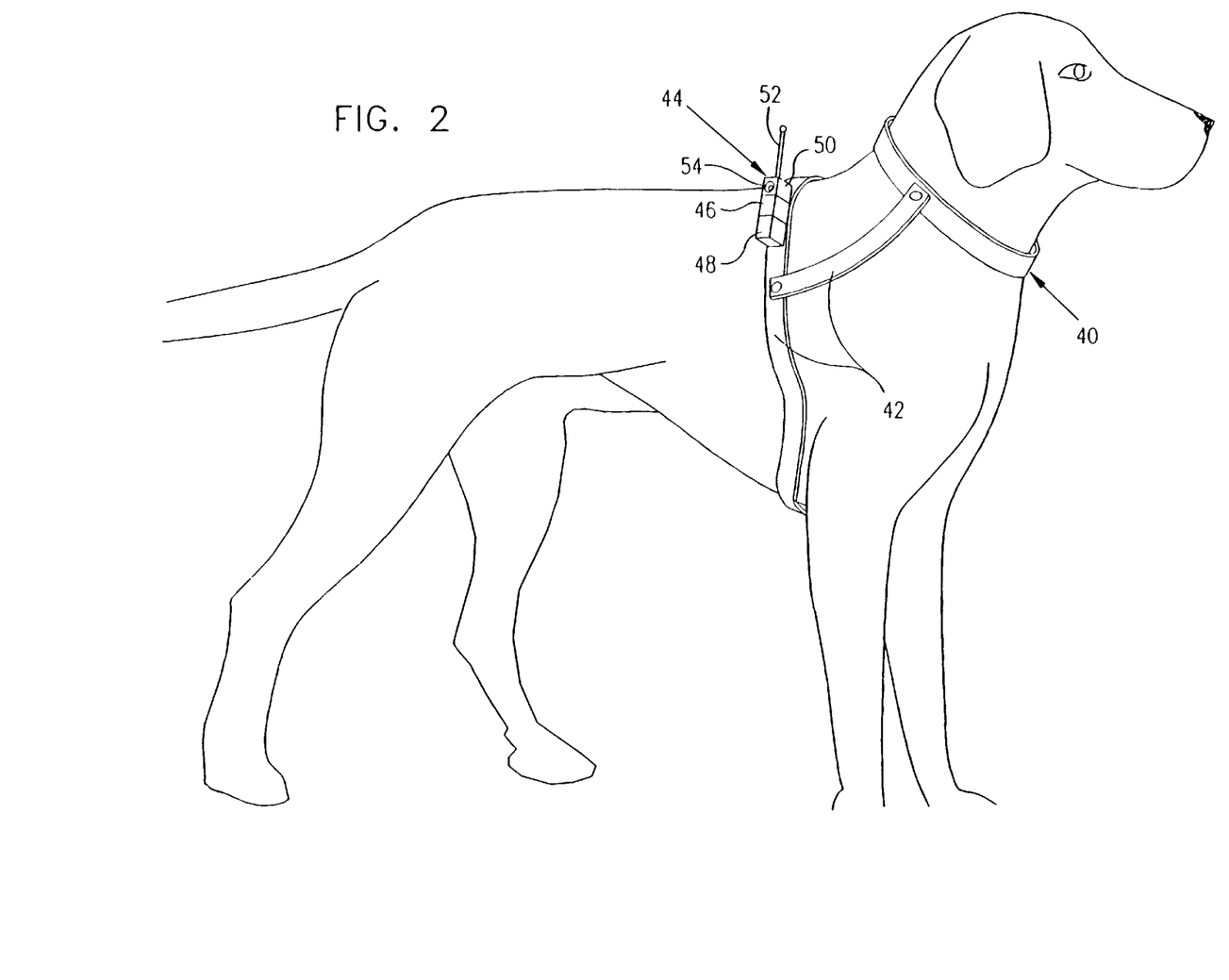
FIG. 2 is a simplified pictorial illustration of a dog wearing a harness constructed and operative in accordance with a preferred embodiment of the present invention.

Reference is now made to FIG. 2, which is a simplified pictorial illustration of a dog wearing a harness 40 constructed and operative in accordance with a preferred embodiment of the present invention. The harness 40 preferably comprises a conventional strap assembly 42 which is fastened about the torso of the dog by conventional means.

In accordance with a preferred embodiment of the invention there is mounted on the strap assembly 42, apparatus 44 for timed dispensing of a pet care substance including an externally pet mounted electronic dispensing controller 46 and a dispenser 48 operated by the electronic dispensing controller 46 for dispensing a pet care substance to the dog at times determined by the electronic dispensing controller 46. In accordance with a preferred embodiment of the present invention, the harness 40 may also include a communication unit 50 including an antenna 52 for permitting wireless communication with the dog and an audio transducer 54, such as a miniature speaker, for providing an audio interface. It is appreciated that the harness may be adapted for any kind of animal or human and the term is to be understood herein to include any kind of belt as well.

Figure 3:
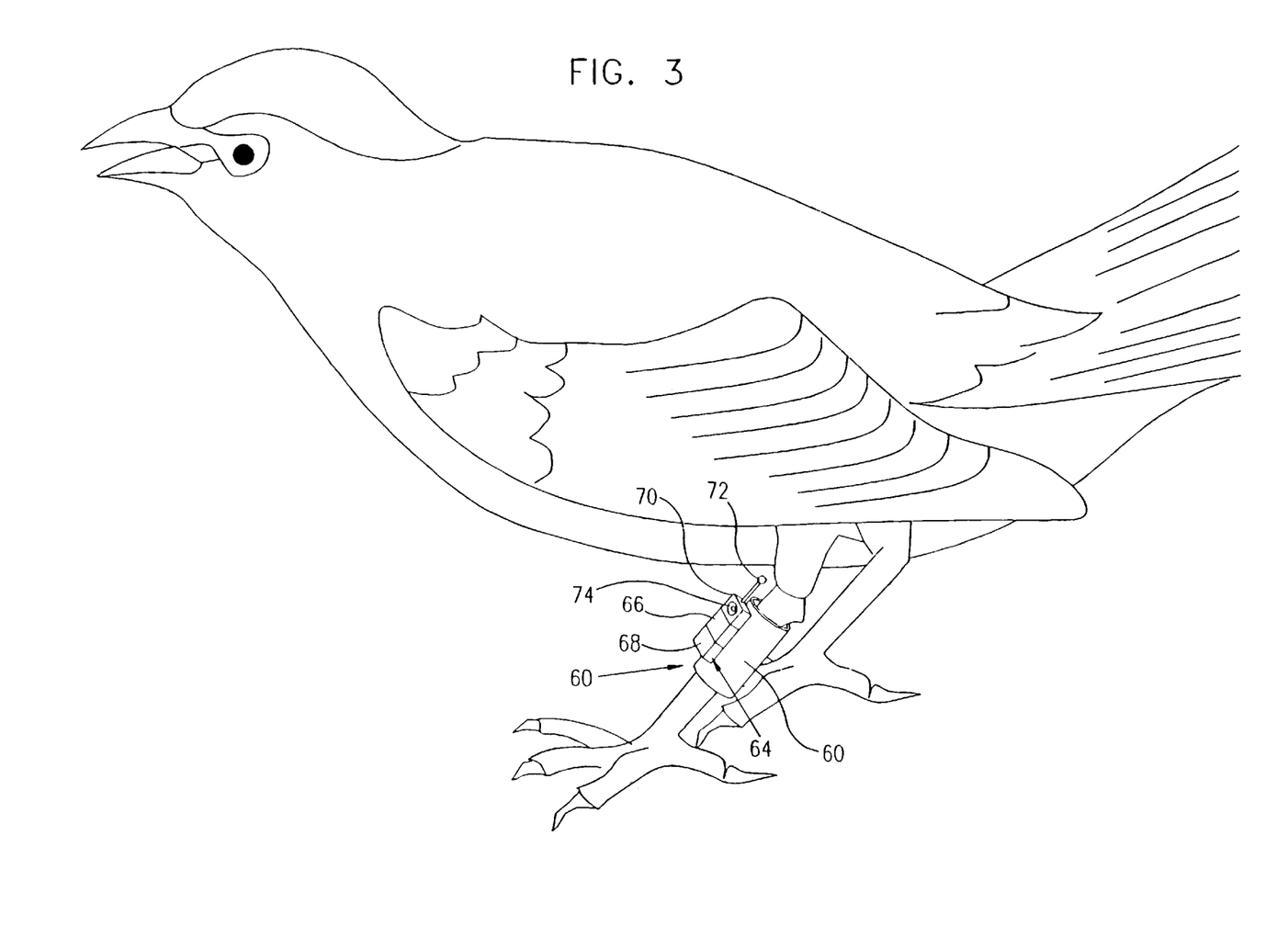
FIG. 3 is a simplified pictorial illustration of a bird wearing a leg bracelet constructed and operative in accordance with a preferred embodiment of the present invention.

Reference is now made to FIG. 3, which is a simplified pictorial illustration of a bird wearing a leg bracelet 60 constructed and operative in accordance with a preferred embodiment of the present invention. The leg bracelet 60 preferably comprises a conventional strap 62 which is fastened about the leg of the bird by conventional means.

In accordance with a preferred embodiment of the invention there is mounted on the strap 62, apparatus 64 for timed dispensing of a pet care substance including an externally mounted electronic dispensing controller 66 and a dispenser 68 operated by the electronic dispensing controller 66 for dispensing a pet care substance to the bird at times determined by the electronic dispensing controller 66. In accordance with a preferred embodiment of the present invention, the bracelet 60 may also include a communication unit 70 including an antenna 72 for permitting wireless communication with the bird and an audio transducer 74, such as a miniature speaker, for providing an audio interface.

It is to be appreciated that the collar is not limited in its application to cats but rather may be used for any other suitable animals, such as livestock. Likewise the harness may be used with any other suitable animal. The leg or arm bracelet may similarly be used, as suitable for animals other than birds.

Figure 4A:
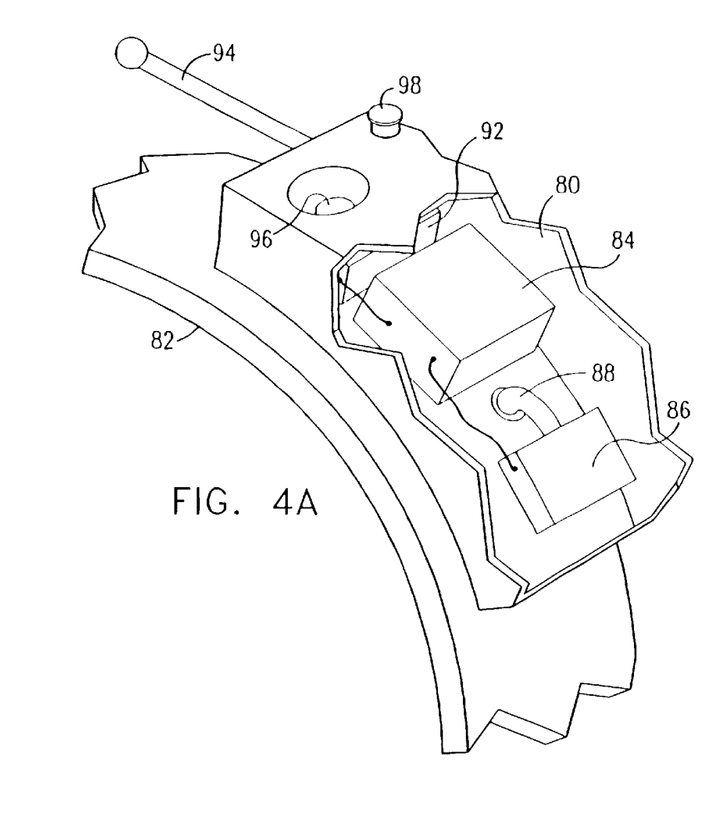
FIGS. 4A and 4B are respective top and bottom simplified, part pictorial, part block diagram illustrations of a collar constructed and operative in accordance with a preferred embodiment of the present invention.
Figure 4B:
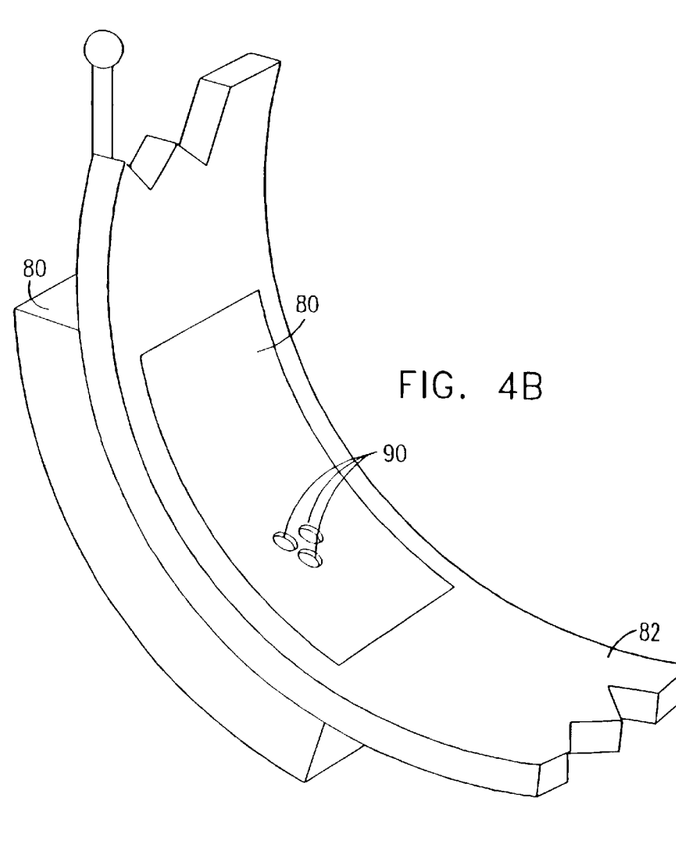

Reference is now made to FIGS. 4A and 4B, which are simplified, part pictorial, part block diagram illustrations of a collar constructed and operative in accordance with a preferred embodiment of the present invention. Here, mounted inside a housing 80 mounted onto a collar strap 82, there is shown an electronic controller 84 which controls the operation of a dispenser 86, having an outlet conduit 88 which preferably communicates with pet care substance outlets 90 on the underside of collar strap 82, in contact with the fur, hair, or skin of an animal wearing the collar. The device may be powered by a conventional power device such as a battery, not shown in FIG. 4A or 4B.

In accordance with a preferred embodiment of the invention, a communications module 92, having an associated antenna 94 and speaker 96 is also provided. Preferably the communications module 92 interfaces with the electronic controller 84, so as to provide various cooperative functionalities, such as lost dog identification annunciation via the speaker 96, using identity information stored in a memory associated with the electronic controller 84. A suitable annunciation actuation button 98 may be provided in association with either communications module 92 or electronic controller 84.

Figure 5:
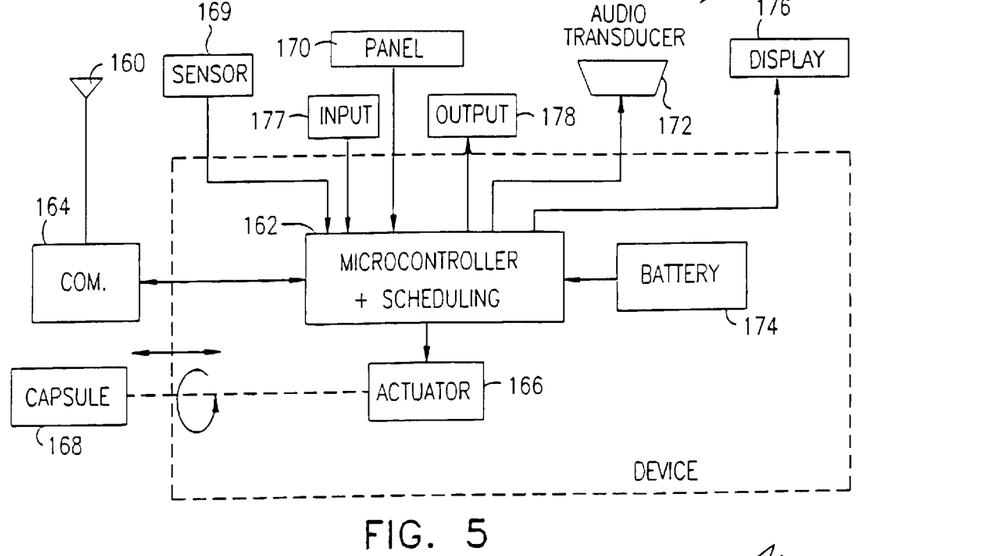
FIG. 5 is a simplified block diagram illustration of apparatus for dispensing pet care substances to pets in accordance with a preferred embodiment of the present invention.

Reference is now made to FIG. 5, which is a simplified functional block diagram illustration of a dispensing and communication device 158 for dispensing pet care substances to pets, and for providing communication with pets in accordance with a preferred embodiment of the present invention. The dispensing and communication device 158 may be typically mounted on animal collars 20, 40 as illustrated in FIGS. 1 and 2 or a leg bracelet 60, as illustrated in FIG. 3.

The dispensing and communication device 158 of FIG. 5 preferably comprises a microcontroller and scheduling unit 162, and an actuator 166 in communication with a capsule 168 containing material for dispensing on to the fur, hair or skin of an animal. The microcontroller 162 typically controls the amount of dispensing material and time at which the material is dispensed.

As illustrated in FIG. 5, the dispensing and communication device 158 also includes a control panel 170 which is in communication with the microcontroller 162. By means of the control panel 170 control signals are provided to the microcontroller 162. Typical control signals may include the amount of dispensing material and the time schedule for dispensing the material to the pet. The dispensing and communication device 158 also comprises a communication unit 164 and an antenna system 160 which provides for one-way or two-way communication and pet location functionalities by wireless communication with the pet. The communication unit 164, connected to the microcontroller 162, allows for the remote control of dispensing material from capsule 168. The wireless connection may employ RF, IR, ultrasound or any other suitable communications medium. The dispensing and communication device 158 may also operate in response to one or more inputs produced by the animal, these inputs being sensed and transmitted to device 158 by a suitable biological sensor 169, such as a sensor for sensing pulse, sweating, breathing, and the like.

The communications unit 164 may also provide lost pet finding functionality in a number of possible ways.

A pet identifying audio message may be stored in the microcontroller 162 and may be played via an audio transducer unit 172 in response to a suitable actuation. Such actuation may be provided by pressing on a suitable actuation button (not shown) mounted onto a control panel 170. Alternatively or additionally a visually sensible message may be stored in the microcontroller 162 and may be displayed on a suitable display 176, such as a liquid crystal display in response to actuation via a suitable actuation button (not shown). A pet identifying message may be displayed on display 176, such messages may typically include the name of the pet, and the address, telephone number, fax number and E-mail address of the owner.

Additionally or alternatively, the communication unit 164 may broadcast a pet locator beacon signal via antenna 160. This beacon signal may be detected by beacon locators, such as those currently used for finding suitably equipped stolen motor vehicles.

As a further alternative or additionally, the system illustrated in FIG. 5 may provide one-way or two-way communication between a pet and its owner, enabling the owner to call its pet via a wireless signal and have the owner's voice output by the audio transducer 172. Similarly, an audio output from the pet may be picked up by audio transducer 172 and transmitted to the owner. Additionally or alternatively, the owner may cause the audio transducer 172 to emit a signal which causes the pet to take a predetermined action, such as to return home or to terminate a given action, such as barking. This signal may be in the form of a high-pitched signal which is only sensible by certain animals and which the pet has been trained to recognize and obey. Instead of a high-pitched signal, any other suitable stimulus, such as an electrical stimulus, may be applied to the pet in response to suitable actuation.

The dispensing and communication device 158 also includes an input device 177 and an output device 178. The input unit 177 allows the recording of information and data by the microcontroller 162, for example by a veterinary expert, to schedule and organize the dispensing of materials, such as medicines, to the pet. Additionally, by means of the input device 177 desired announcements and reminders may be recorded in the microcontroller 162.

The output device 178 allows the retrieving of the data and information from the microcontroller 162 in order to provide a schedule and record of the treatment of the pet carried out over a given period of time. Additionally, the output device 178 may retrieve all relevant information regarding the pet and its activities.

The dispensing and communication device 158 preferably also includes a power device, such as a battery 174. Alternatively, the power device may include an animal driven power generator, such as a dynamo driven by a running action of the animal, for example.

Figure 6:
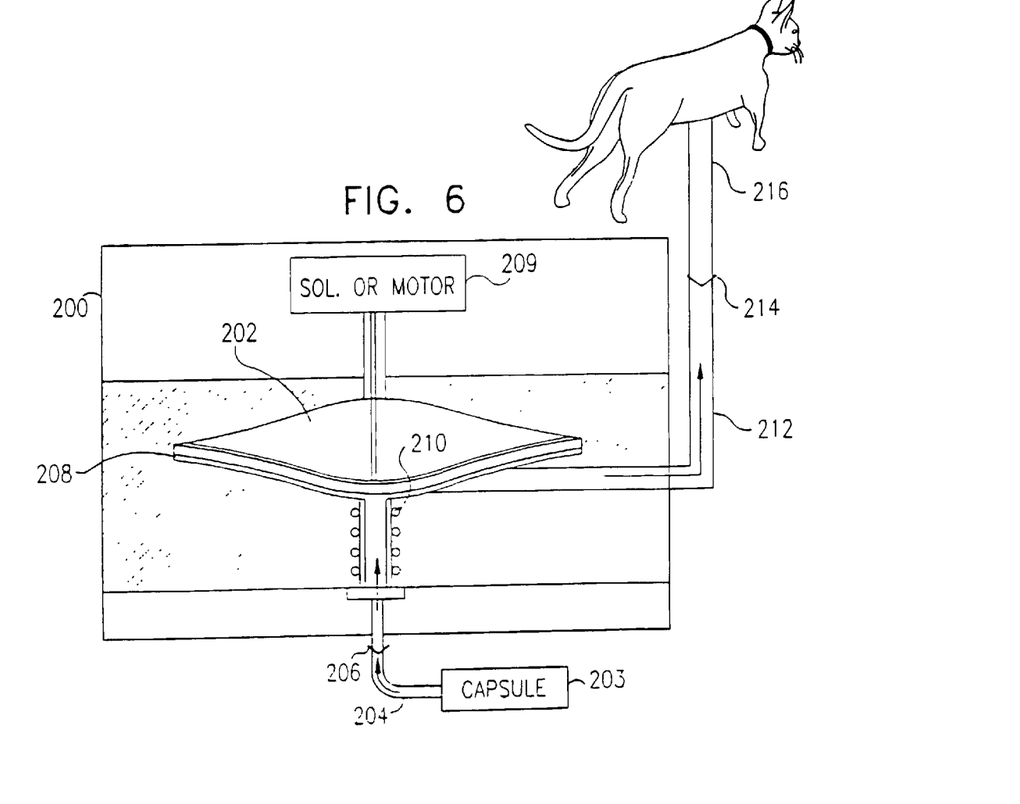
FIG. 6 is a simplified illustration of a pump assembly constructed and operative in accordance with one embodiment of the present invention, which is useful in the apparatus of FIGS. 1–5.

Reference is now made to FIG. 6, which is a simplified illustration of a pump assembly constructed and operative in accordance with one embodiment of the present invention, which is useful in the apparatus of FIGS. 1–5. It is appreciated that the pump assembly described with reference to FIG. 6, as well as those described with reference to FIGS. 7 and 8, may be fashioned for internal or external use with the patient/animal. It is also appreciated that one or more valves may be used instead of any of the pump assemblies.

The pump of FIG. 6 comprises a housing 200 defining an enclosure 202 which communicates with supply module or capsule 203 via an inlet conduit 204, preferably having a one-way valve 206. A diaphragm 208 is disposed within enclosure 202 and may be spring loaded by a spring 210. By periodically displacing the diaphragm 208 within the enclosure 202, by means of a solenoid device or motor 209, fluid from the capsule supply 203 is drawn into enclosure 202 and subsequently the fluid is forced out of enclosure 202 via an outlet conduit 212, also preferably having a one-way valve 214. The outlet conduit 212 preferably communicates via a conduit 216 with a dispensing outlet (not shown). Preferably, the dispensing outlet is located on the underside of a strap (not shown), in contact with the fur, hair, or skin of an animal wearing the collar. The dispensing outlet may be located such that the fluid is dispensed on a dorsal location on the pet. Alternatively, the fluid may be dispensed directly onto the skin of the pet or may dispensed for licking by the pet.

The pet care substance from capsule supply 203 may include any kind of substance useful in the care of animals such as an anti-parasitic agent, a pet grooming material, an veterinary therapeutic agent or a male animal repellent, or any kind of medical treatment or even cosmetic substance.

Figure 7:
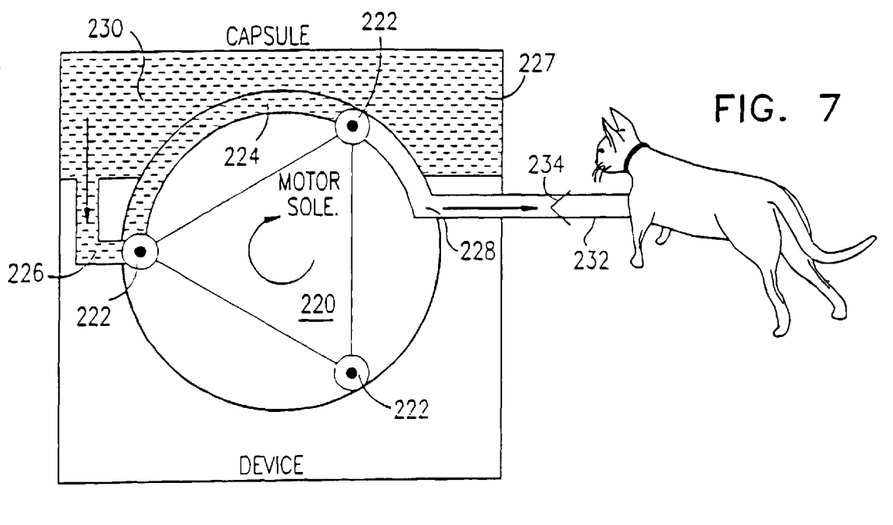
FIG. 7 is a simplified illustration of a pump assembly constructed and operative in accordance with another embodiment of the present invention, which is useful in the apparatus of FIGS. 1–5.

Reference is now made to FIG. 7, which is a simplified illustration of a pump assembly constructed and operative in accordance with another embodiment of the present invention, which is useful in the apparatus of FIGS. 1–5. The pump of FIG. 7, is commonly termed a peristaltic pump and preferably comprises a rotor 220 having a plurality of rollers 222 mounted thereon for sequential progressive squeezing travel along a resilient conduit 224 extending from an inlet 226, coupled to supply module 227, to an outlet 228. The rotation of rotor 220 produces metered dispensing of a fluid substance 230 via a conduit 232 and a one-way valve 234 to a dispensing outlet (not shown). Preferably, the dispensing outlet is located on the underside of a strap (not shown), in contact with the fur, hair, or skin of an animal wearing the collar.

Figure 8:
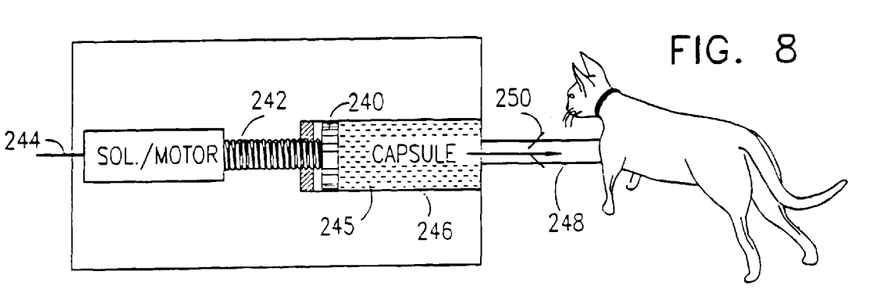
FIG. 8 is a simplified illustration of a combination pump assembly and supply module constructed and operative in accordance with yet another embodiment of the present invention, which is useful in the apparatus of FIGS. 1–5.

Reference is now made to FIG. 8, which is a simplified illustration of a combined supply module and pump assembly constituting a replaceable dispensing subsystem, constructed and operative in accordance with yet another embodiment of the present invention, which is useful in the apparatus of FIGS. 1–5. Here a piston 240 attached to a threaded shaft 242 is arranged to move along an axis 244, thereby causing continuous dispensing of a fluid substance 245 contained in a cylinder 246, downstream of the piston 240. The movement of piston 240 produces metered dispensing of fluid substance 245 via a conduit 248 and a one-way valve 250 to a dispensing outlet (not shown). Preferably, the dispensing outlet is located on the underside of a strap (not shown), in contact with the fur, hair, or skin of an animal wearing the collar.

Figure 9:
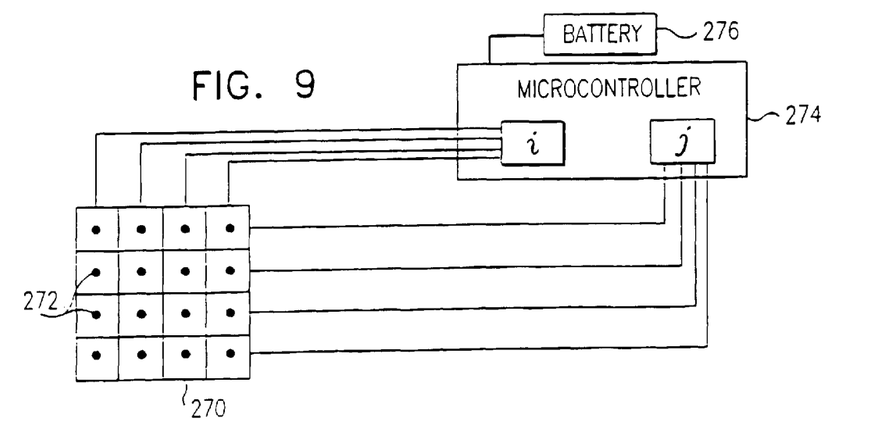
FIG. 9 is a simplified illustration of a dispensing assembly constructed and operative in accordance with a further preferred embodiment of the present invention.

FIG. 9 is a simplified illustration of a dispensing assembly constructed and operative in accordance with a further preferred embodiment of the present invention. In this embodiment, predetermined amounts of a pet care substance are contained in a multiplicity of cell enclosures 270 located in communication with the fur, hair, or skin of an animal wearing a collar or harness. Each enclosure 270 is permeable for release of the substance contained therein in response to an electrical signal which may be supplied by dispensing and communication device 158 or alternatively by a driver (not shown) controlled thereby. It is noted that cell enclosures 270 may contain the same substance or they may contain different substances. Each substance may be a pure substance or a mixture of substances. The cell enclosures 270 may be of the same size or of varying sizes.

In one embodiment of the present invention, each cell enclosure (i, j) 270 is formed with an electrode or electrical resistance heating element 272 which is heated by application of electrical energy thereto and causes that all of the cell enclosure 270 to break, melt, disintegrate or otherwise become permeable to the care substance, thereby allowing the care substance contained therein to reach the pet. By discrete application of electrical energy to individual cell enclosures 270 predetermined quantities of the care substance are supplied with predetermined timing to the pet. The supply of electrical energy to the cell enclosures 270 is preferably regulated by a microcontroller 274, receiving power from a battery 276.

In accordance with a preferred embodiment of the present invention, the apparatus of FIG. 9 is disposable and readily replaceable. The apparatus of FIG. 9 may be constructed for single-use or multi-use. In the latter case, either cell enclosures 270 are refillable or one can replace the entire array of enclosures.

It is noted that electrical energy is just one example of using energy to make the cell enclosures 270 permeable for passage therethrough of the substance contained therein. In general, it can be said that the dispensing assembly includes release apparatus which comprises an energizing element associated with each of the cell enclosures and operative, when energized, to cause at least a portion of the cell enclosure to become permeable for passage therethrough of the substance contained therein.

Figure 10:
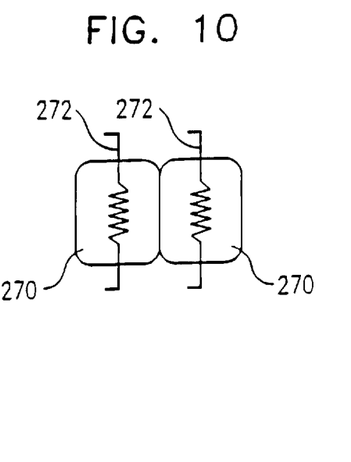
FIG. 10 is a simplified illustration of assembling electrical resistance heating elements with cell enclosures, useful in the dispensing assembly of FIG. 9, in accordance with one preferred embodiment of the present invention.

FIG. 10 illustrates one example of assembling electrical resistance heating elements 272 with cell enclosures 270. In this embodiment, electrical resistance heating element 272 is embedded or attached in each cell enclosure 270.

Figure 11A:
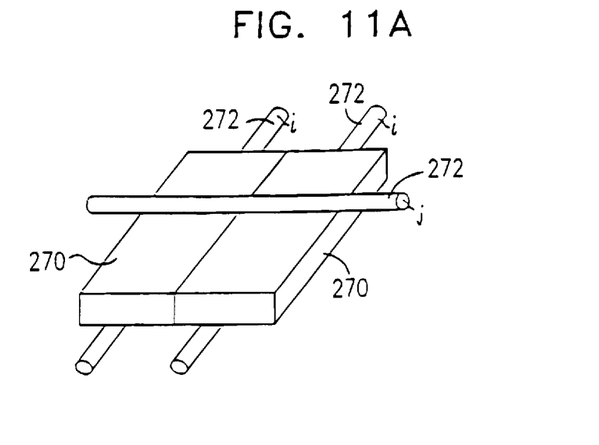
FIGS. 11A–11C are simplified illustrations of assembling electrical resistance heating elements with cell enclosures, useful in the dispensing assembly of FIG. 9, in accordance with another preferred embodiment of the present invention.
Figure 11B:
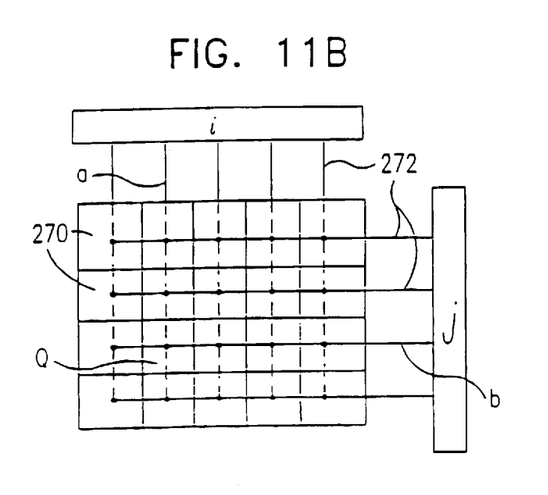
Figure 11C:
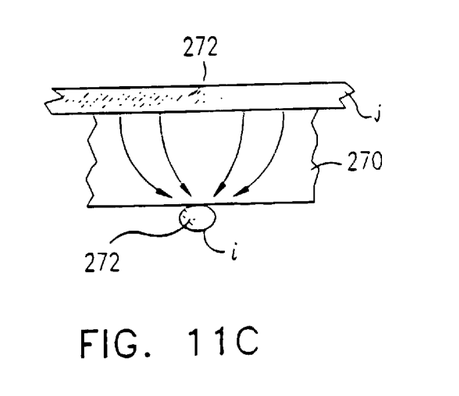

Reference is now made to FIGS. 11A–11C which illustrate another method of assembling electrical resistance heating elements 272 with cell enclosures 270. In this embodiment, i columns of electrical resistance heating elements 272 are arranged to contact the bottom surfaces of cell enclosures 270 and j rows of electrical resistance heating elements 272 are arranged to contact the top surfaces of cell enclosures 270. Suppose it is desired to energize a particular cell Q corresponding to i=a and j=b. In the embodiment of FIGS. 11A and 11B, this is easily accomplished by passing a current through the a column heating element and the b row heating element. As seen in FIG. 11C, the flow of electric current between the row and column heating elements energizes the cell and makes the cell permeable to the fluid contained therein as described hereinabove. The cell enclosure itself, and/or the contents thereof, acts as an electrical resistance element.

In the illustrated embodiment of FIGS. 11A–11C, only 9 electrical contacts are required to energize 20 cells. In contrast, in the embodiment of FIG. 9 wherein each cell is individually energized, 20 separate electrical contacts would have to be used to energize the 20 cells.

Figure 11D:
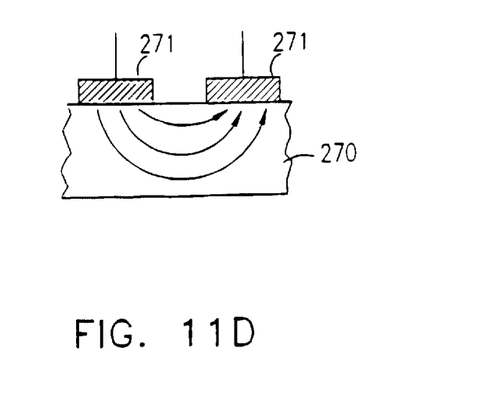
FIG. 11D is a simplified illustration of assembling electrical resistance heating elements with cell enclosures, useful in the dispensing assembly of FIG. 9, in accordance with yet another preferred embodiment of the present invention.

FIG. 11D illustrates another method of wherein a pair of electrodes 271 are placed on top of cell enclosure 270 and current flows through cell enclosure 270 itself. It is appreciated by persons skilled in the art, that many other methods may be used to energize the cells.

Figure 12A:
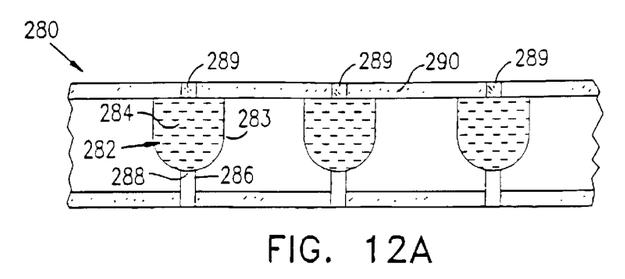
FIGS. 12A and 12B are simplified sectional illustrations of a dispensing assembly, before and after dispensing of a pet care substance, respectively, constructed and operative in accordance with still another preferred embodiment of the present invention, wherein a fluid pet care substance is vacuum-packed in a cell, such as a microcell.
Figure 12B:
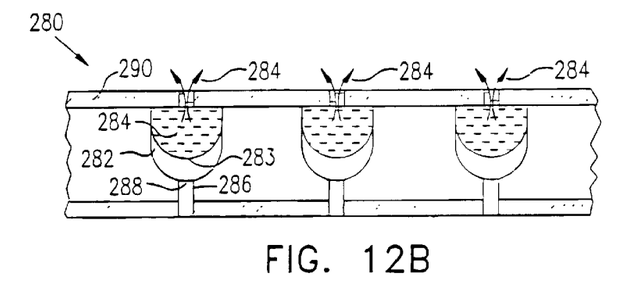

Reference is now made to FIGS. 12A and 12B which illustrate a dispensing assembly 280 constructed and operative in accordance with still another preferred embodiment of the present invention. Assembly 280 preferably includes a plurality of cells 282, which may be of any suitable dimension, such as, but not necessarily, microcells with a diameter of several microns. A fluid substance 284 is preferably vacuum-packed in cell 282 in the following manner. Cell 282 is lined with a membrane 283 which is preferably resilient. Each cell 282 is formed with a conduit 286 which is in fluid communication with cell 282 at a junction 288. A flexible membrane 283 is initially placed over the cells 282 and suction is applied to cells 282 via conduits 286. The sucking force of the applied suction draws the membrane 283 tightly into each cell 282, so that each cell 282 is lined with membrane 283, this being the configuration shown in FIG. 12A. Cells 282 are then filled with fluid substance 284 and a cover sheet 290 is finally placed over cells 282 at the end opposite to junctions 288. Cover sheet 290 and membrane 283 seal fluid substance 284 in cells 282.

Cover sheet 290 is formed with a plurality of rupturable openings 289 each of which is in electrical communication with a heating element, as described hereinabove with reference to FIGS. 9–11D, so that upon appropriate energizing, rupturable openings 289 open to permit flow therethrough of fluid substance 284.

As seen in FIG. 12B, since membrane 283 has been drawn into tension by the initial suction force, opening rupturable opening 289 releases the tension in membrane 283 and causes fluid substance 284 to gush out of cell 282 with a velocity significantly higher than that shown in previous embodiments. It is appreciated that other devices other than membrane 283 may be used to propel fluid substance 284 out of cells 282, such as a piston, solenoid, pressurized air or fluid, compressible or spongy material, and the like.

Figure 13:
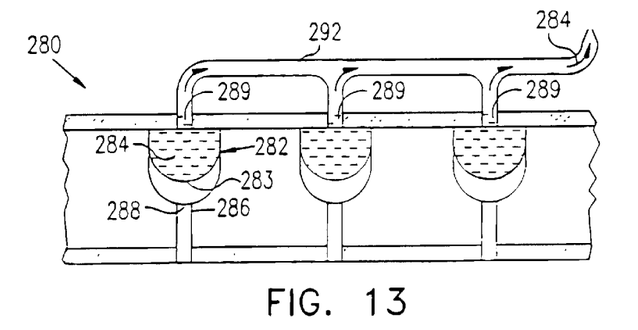
FIG. 13 is a simplified sectional illustration of a dispensing assembly, constructed and operative in accordance with yet another preferred embodiment of the present invention, wherein the fluid substance is dispensed via a manifold in fluid communication with a plurality of cells.

In FIG. 13, assembly 280 is modified such that fluid substance 284 is dispensed via a manifold 292 in fluid communication with the plurality of rupturable openings 289. Such an embodiment may be useful in directing fluid substance 284 to a particular location on the pet or for concentrating the flow of fluid substance 284.

Figure 14A:
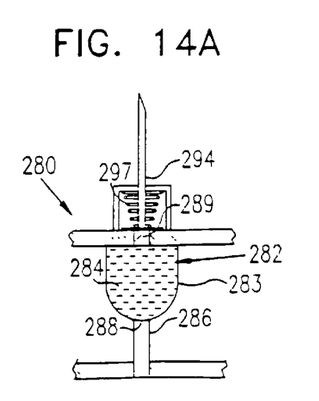
FIGS. 14A and 14B are simplified illustrations of a dispensing assembly, before and after dispensing of a pet care substance, respectively, constructed and operative in accordance with another preferred embodiment of the present invention, wherein a fluid pet care substance is dispensed via a needle.
Figure 14B:
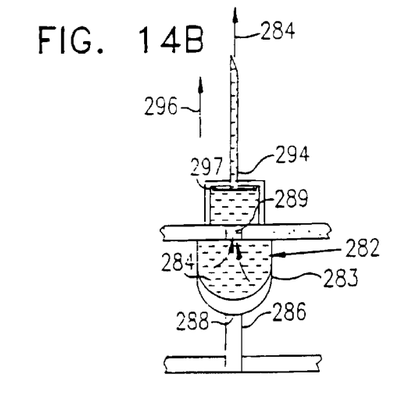

In FIGS. 14A and 14B, a further modification of dispensing assembly 280 is shown. In this embodiment, cell 282 is formed with a needle 294 which is in fluid communication with and extends from rupturable opening 289. Upon rupturing the rupturable opening 289, as seen in FIG. 14B, fluid substance 284 gushes out of cell 282. The force of the expelled fluid substance propels needle 294 generally in the direction of an arrow 296 which may cause needle 294 to pierce the skin of a patient/animal. Needle 294 may be hollow, in which case fluid 284 flows through needle 294 and into the body of the patient. Alternatively, needle 294 may be non-hollow, in which case, fluid 284 flows over the outer surface of needle 294. It is noted that needle 294 need not pierce the skin, but instead needle 294 may act like teeth of a comb which press against or stroke the skin/fur of the patient/animal. Preferably, needle 294 is biased by a biasing device 297, such as coil springs, so as to retract needle 294 after injection. Of course, other devices may be used to retract needle 294.

As described above with reference to FIGS. 10–11D, the dispensing assembly of the present invention includes release apparatus which comprises an energizing element associated with each of the cell enclosures and operative, when energized, to cause at least a portion of the cell enclosure to become permeable for passage therethrough of the substance contained therein. A release apparatus of this nature may be incorporated in the embodiments of FIGS. 12A, 12B and 13, as is now described with reference to FIGS. 21A and 21B.

Figure 21A:
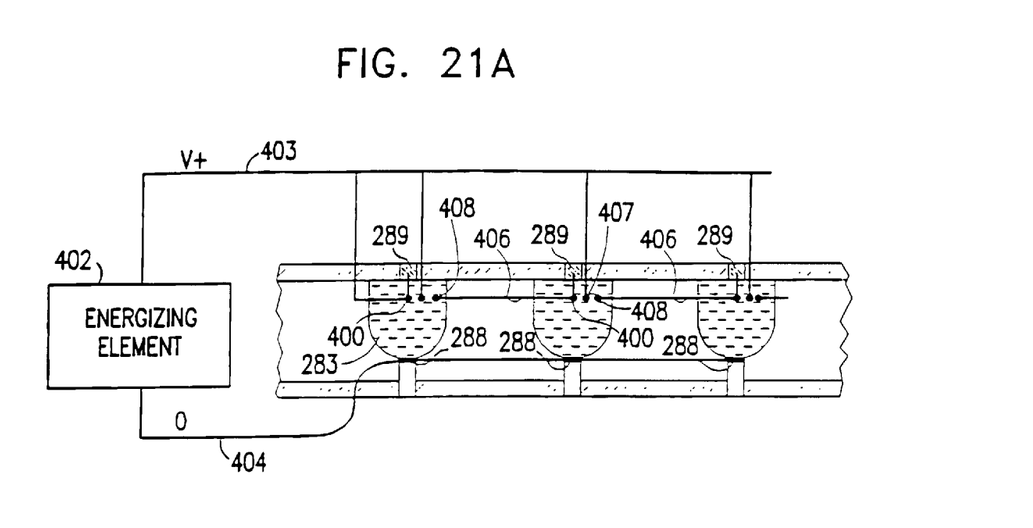
FIGS. 21A and 21B are simplified illustrations of a membrane acting as an electrical switch in a dispenser and an electronic dispensing controller, constructed and operative in accordance with still another preferred embodiment of the present invention.
Figure 21B:
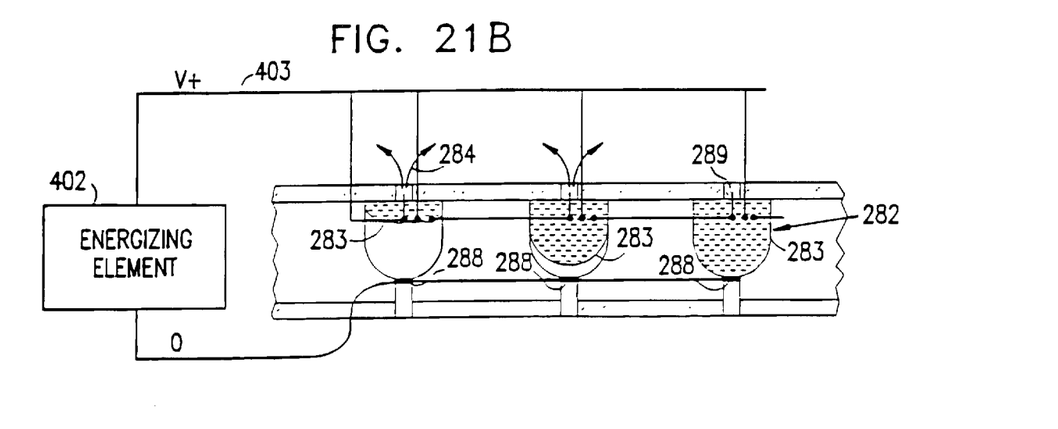

Rupturable opening 289 of the first cell 282 is in electrical contact with an electrode 400 which is connected to an energizing element 402 (preferably an electrical power source) via a positive voltage lead 403. Energizing element 402 is only connected to the first cell 282 at electrode 400. In contrast, a ground lead 404 of energizing element 402 is connected to all the junctions 288 of the cells 282, the junctions in this embodiment being electrical contacts. In this embodiment, membrane 283 is made of an electrically conducting material. The electrodes 400 of the rupturable openings 289 of the cells 282 following the first cell, are each connected by a wire 406 to a contact 408 in the previous cell.

As seen in FIG. 21A, when cell 282 is completely full prior to rupturing of rupturable opening 289, membrane 283 contacts junction 288. Energizing element 402 can then send an electrical current to electrode 400 of the first cell only and caused rupture thereof. After membrane 283 completely expels fluid substance 284 from the first cell 282, membrane 283 then contacts electrode 400 and contact 408 in first cell 282. Only then can an electrical current be passed to the second cell 282. Thus, the membrane of the previous cell acts as a switch to switch electricity to enable rupturing of the subsequent cell. Preferably, suitable circuitry is provided to sense the drop in voltage or current due to the movement of the membrane away from junction 288 so that energizing element 402 can be signaled to stop supplying unnecessary voltage to electrode 400. This circuitry serves as a feedback for proper operation of the release apparatus.

Any of the dispensers and electronic dispensing controllers of the present invention may be packaged and configured in a variety of manners for easy use by a patient/animal. Some examples are now described with reference to FIGS. 15–20.

Figure 15:
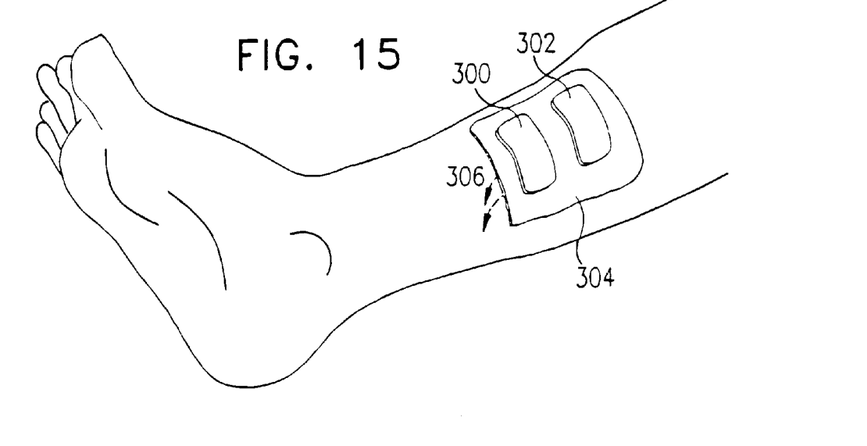
FIG. 15 is a simplified illustration of a dispenser and an electronic dispensing controller, constructed and operative in accordance with a preferred embodiment of the present invention, wherein the dispenser and electronic dispensing controller are mounted on a bandage patch attachable to a patient/animal.

Reference is now made to FIG. 15 which illustrates a dispenser 300 and an electronic dispensing controller 302, constructed and operative in accordance with a preferred embodiment of the present invention. Dispenser 300 and electronic dispensing controller 302 are mounted on a bandage patch 304 attachable to a patient/animal. Such an embodiment may be particularly useful in dispensing a transdermal substance 306.

Figure 16:
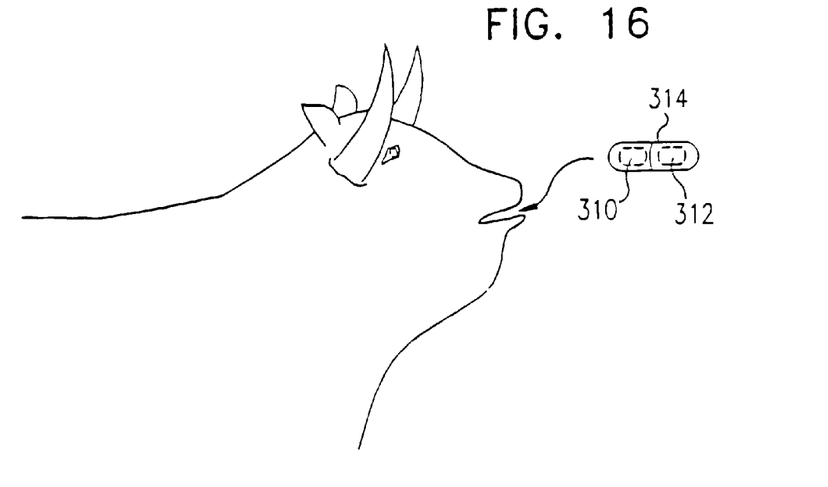
FIG. 16 is a simplified illustration of a dispenser and an electronic dispensing controller, constructed and operative in accordance with another preferred embodiment of the present invention, wherein the dispenser and electronic dispensing controller are packaged as a bolus.

Reference is now made to FIG. 16 which illustrates a dispenser 310 and an electronic dispensing controller 312, constructed and operative in accordance with another preferred embodiment of the present invention. Dispenser 310 and electronic dispensing controller 312 are packaged as a bolus 314, i.e., a pill or tablet used in veterinary or clinical medicine. In this embodiment, dispenser 310 and electronic dispensing controller 312 operate as long as they are present in the stomach or other portions of the alimentary canal, and cease to operate upon expelment from the body. Alternatively, dispenser 310 and electronic dispensing controller 312 may be fashioned to remain in the body.

Figure 17:
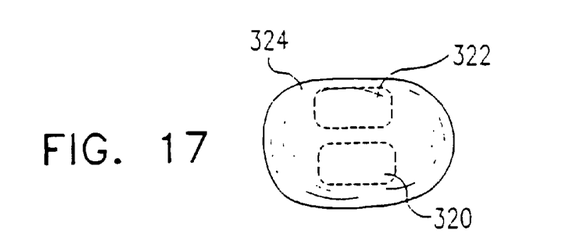
FIG. 17 is a simplified illustration of a dispenser and an electronic dispensing controller, constructed and operative in accordance with yet another preferred embodiment of the present invention, wherein the dispenser and electronic dispensing controller are packaged in an expandable balloon which is adapted for expanding in a stomach of a patient/animal.

Reference is now made to FIG. 17 which illustrates a dispenser 320 and an electronic dispensing controller 322, constructed and operative in accordance with yet another preferred embodiment of the present invention. Dispenser 320 and electronic dispensing controller 322 are packaged in an expandable balloon 324 which is adapted for expanding in a stomach of a patient/animal. The possible operations of dispenser 320 and electronic dispensing controller 322 are as described previously for dispenser 310 and electronic dispensing controller 312.

Figure 18:
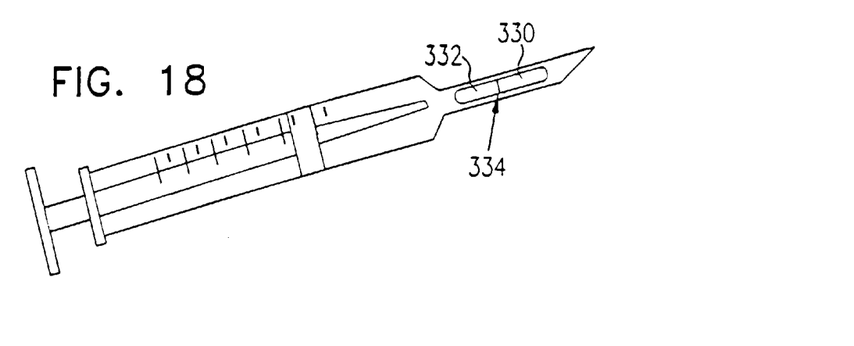
FIG. 18 is a simplified illustration of a dispenser and an electronic dispensing controller, constructed and operative in accordance with still another preferred embodiment of the present invention, wherein the dispenser and electronic dispensing controller are themselves injectable into a patient/animal.

Reference is now made to FIG. 18 which illustrates a dispenser 330 and an electronic dispensing controller 332, constructed and operative in accordance with still another preferred embodiment of the present invention. Dispenser 330 and electronic dispensing controller 332 are packaged as a projectile 334 which is injectable into a patient/animal.

Figure 19:
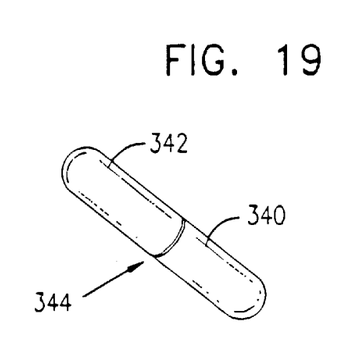
FIG. 19 is a simplified illustration of a dispenser and an electronic dispensing controller, constructed and operative in accordance with another preferred embodiment of the present invention, wherein the dispenser and electronic dispensing controller are themselves implantable into a patient/animal.

Reference is now made to FIG. 19 which illustrates a dispenser 340 and an electronic dispensing controller 342, constructed and operative in accordance with another preferred embodiment of the present invention. Dispenser 340 and electronic dispensing controller 342 are packaged as a module 344 implantable into a patient/animal.

Figure 20:
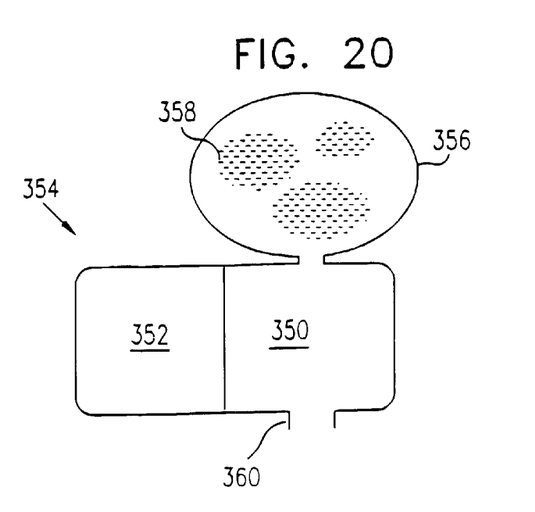
FIG. 20 is a simplified illustration of a dispenser and an electronic dispensing controller, constructed and operative in accordance with yet another preferred embodiment of the present invention, wherein the dispenser and electronic dispensing controller comprise a Micro-Electro-Mechanics Systems (MEMS) pump.

Reference is now made to FIG. 20 which illustrate a dispenser 350 and an electronic dispensing controller 352, constructed and operative in accordance with yet another preferred embodiment of the present invention. Dispenser 350 and electronic dispensing controller 352 comprise a Micro-Electro-Mechanics Systems (MEMS) pump 354.

As is known in the art of MEMS, MEMS are fabricated from metals such as aluminum, tungsten, nickel, etc. In addition, MEMS are fabricated from polycrystal materials such as polysilicon and single crystal (SC) materials such as Single Crystal Silicon (SCS).

MEMS pump 354 is preferably in fluid communication with a reservoir 356 of a substance 358. MEMS pump 354 pumps the substance 358 via an outlet port 360, the pumping being controlled by controller 352. MEMS pump 354 is thus an "on-chip" pump with all the necessary electronic pump controls built into the chip. Controller 352, as well as any of the control devices of the previously described embodiments of the present invention, may be programmable and may be connected to an external input/output (I/O) device. The I/O device can feed instructions and data to the controller and can receive data from the controller for processing with a computer such as a PC.

It will be appreciated by persons skilled in the art that the present invention is not limited to what has been particularly shown and described hereinabove. Rather the scope of the present invention also includes both combinations and sub-combinations of the various features described and shown hereinabove as well as modifications and further developments thereof which would occur to persons skilled in the art upon reading the above description and which are not already in the prior art.

What is claimed is:

1. A dispensing assembly comprising:
   a dispensing controller (158); and
   a dispenser operated by said dispensing controller (158) for dispensing a substance at times determined by said dispensing controller (158),
   and wherein said dispenser comprises:
   at least one discrete container cell (270, 282) having an enclosure material and containing said substance; and
   release apparatus, responsive to said dispensing controller (158), for selectably releasing said substance from said at least one container cell (270, 282) in a desired timed pattern, determined by said dispensing controller (158);
   characterized by said release apparatus comprising an energizing element connected to said at least one cell (270, 282), said energizing element producing an electrical current which flows to said enclosure material of said at least one cell (270, 282), wherein said electrical current itself changes a characteristic of a portion of the enclosure material so as to make it permeable for passage therethrough of said substance.

2. The dispensing assembly according to claim 1 wherein the electrical current electrically heats the portion of the enclosure material of said at least one cell (270, 282).

3. The dispensing assembly according to claim 1 wherein the electrical current melts the portion of the enclosure material of said at least one cell (270, 282).

4. The dispensing assembly according to claim 1 wherein the electrical current disintegrates the portion of the enclosure material of said at least one cell (270, 282).

5. The dispensing assembly according to claim 1 wherein an electrical wire (272) is attached to said enclosure material of said at least one cell (270, 282).

6. The dispensing assembly according to claim 1 wherein an electrical wire (272) is disposed trough said at least one cell (270, 282).

7. The dispensing assembly according to claim 1 wherein the electrical current passes through said enclosure material.

8. The dispensing assembly according to claim 1 wherein the electrical current changes a material property of said enclosure material such that said enclosure material becomes permeable for passage therethrough of said substance.

9. The dispensing assembly according to claim 7 wherein said substance acts as an electrical resistance element.

10. The dispensing assembly according to claim 1 further characterized by said release apparatus comprising i columns of a plurality of such energizing elements (272) arranged to contact bottom surfaces of said cells (270) and j rows of a plurality of such energizing elements (272) arranged to contact top surfaces of said cells (270).

11. A dispensing assembly (280) comprising:

an dispensing controller; and a dispenser operated by said dispensing controller for dispensing a substance (284) at times determined by said dispensing controller, and wherein said dispenser comprises:

a plurality of discrete container cells (282), each containing said substance (284); and release apparatus, responsive to said dispensing controller, for selectably releasing said substance (284) from individual ones of said container cells (282) in a desired timed patter, determined by said dispersing controller;

characterized in that each said discrete container cell (282) comprises a propelling device, which upon actuation of said release apparatus, propels said substance (284) out of said cell (282), wherein said propelling device comprises a membrane (283) initially in tension, and wherein the membrane (283) of a previous cell (282) acts as a switch to switch electricity to enable rupturing of a subsequent cell (282).

12. The dispensing assembly (280) according to claim 11 and further comprising a manifold (292) in fluid communication with said cells (282).

13. The dispensing assembly (280) according to claim 11 further comprising back circuitry which senses movement of the membrane (283) to regulate operation of the release apparatus.

* * * * *